United States Patent [19]  [11]  4,202,033
Strobel  [45]  May 6, 1980

[54] APPARATUS AND METHOD UTILIZING CALCULATOR FOR QUALITY CONTROL OF HEMATOLOGY SAMPLE ANALYSIS

[75] Inventor: Stanley W. Strobel, San Carlos, Calif.

[73] Assignee: Royco Instruments, Inc., Menlo Park, Calif.

[21] Appl. No.: 864,282

[22] Filed: Dec. 27, 1977

[51] Int. Cl.² ...................... G06F 15/42; G01N 33/16
[52] U.S. Cl. ..................................... 364/416; 364/571
[58] Field of Search ................................ 364/416, 571

[56] References Cited

U.S. PATENT DOCUMENTS

| 3,634,868 | 1/1972 | Pelavin et al. | 364/416 X |
| 3,686,486 | 8/1972 | Coulter et al. | 364/416 X |
| 3,920,970 | 11/1975 | Slaker | 364/571 X |
| 4,061,469 | 12/1977 | DuBose | 364/416 X |
| 4,071,891 | 1/1978 | Barrows | 364/416 |

Primary Examiner—David H. Malzahn
Attorney, Agent, or Firm—Robert P. Cogan

[57] ABSTRACT

A method and apparatus monitor calibration of a hematology parameter measurement system. A baseline control value measured on an unassayed sample is entered and stored in a register in a calculator. Sample parameter measurements are entered in the calculator, and a prior art "moving averages" method is used to calculate a "moving averages" value indicative of calibration drift. After a preselected time or number of sample measurements, the same unassayed sample is again measured. The measurement is entered. Calibration status is monitored by comparison of the sample measurements and by comparison of the moving averages value to a preselected threshold level.

6 Claims, 5 Drawing Figures

APPARATUS AND METHOD UTILIZING CALCULATOR FOR QUALITY CONTROL OF HEMATOLOGY SAMPLE ANALYSIS

BACKGROUND OF THE INVENTION

The present invention relates to an apparatus and method utilizing a calculator and register means for monitoring calibration for quality control of hematology sample analysis.

The basic hematology measurement, means are provided for measuring such hematological parameters as red blood cell count, white blood cell count and hemoglobin or diluted blood samples. Further parameters which may be measured include mean corpuscular volume and hematocrit. Additional useful parameters which may be calculated either automatically or based on other readings are mean corpuscular hemoglobin (MCH) and mean corpuscular hemoglobin concentration (MCHC). Each parameter is of diagnostic significance. Commonly known electronic instruments for measuring parameters must be initially calibrated, and calibration must be monitored to assure that electronic signals indicative of measured parameters are within allowable limits of precision. Instrumentation results, namely measured values for given inputs, can vary in the course of operation.

Commonly, calibration on a hematology parameter measuring instrument is maintained by calibrating the instrument to a standard and periodically running control samples after the testing of predetermined numbers of patient samples. This commonly applied approach, while reliable and satisfactory, is expensive. Further, the assay sheet accompanying a control reagent tells the operator in advance what to expect. The running of controls requires the operational effort of testing additional samples as well. Occasionally, instability of standards or controls can lead to a false indication of loss of calibration.

In order to monitor calibration of a hematology measurement instrument at frequent periodic intervals without the use of control samples, a prior art method referred to herein as the "moving average method" has been developed. This method is known in the art and is explained, for example, in B. S. Bull et al, "A Study of Various Estimators for the Derivation of Quality Control Procedures from Patient Erythrocyte Indices," American Journal of Clinical Pathology, Vol. 61, No. 4, April 1974, pp. 473-481. It has been found that of all the parameter values obtained for hematology samples, both MCV and MCHC are parameters to whose values it is preferred to apply estimator functions for monitoring whether values obtained are within calibration limits. The estimator functions may be applied to values obtained for groups of samples even though the samples are drawn from hospital patients who are in all probability hematologically sick. One such estimator is called by Bull et al $X_B$ and named the alternative moving average.

$$\overline{X}_{B,i} = (2-r)\overline{X}_{B,i-1} + rd$$

where $X_{B,i}$ is the estimator of the true mean after $i$ batches of patient samples have been measured and $X_{B,i-1}$ is the estimator after $(i-1)$ batches, $r$ is greater than zero and less than or equal to 1, and d is some sign function equal to plus or minus one or equal to zero, depending on whether or not a particular value $X_j$ within batch $i$ is greater than, equal to, or less than the value $\overline{X}_{B,i-1}$. The function $$d = sgn\left(\sum_{j=1}^{N} sgn(X_j - \overline{X}_{B,i-1})|X_j - \overline{X}_{B,i-1}|^P\right) \times$$

$$\left(\sum_{j=1}^{N} \frac{sgn(X_j - \overline{X}_{B,i-1})|X_j - \overline{X}_{B,i-1}|^P}{N}\right)^{1/P}$$

where $P = \frac{1}{2}$ and N is the number of samples in the batch. This value may be calculated on a programmable calculator. Use of this function for the average value of a parameter MCV or MCHC should transform raw laboratory data indicative of the values of averages within successive batches into a relatively flat curve. If the curve departs by a preselected amount from a baseline value for the curve, then the condition of the instrument being out of calibration is indicated, and the operator may adjust calibration of the instrument. It should be noted that in the present context, the term "moving average method" is used to mean a method in which an estimator function is applied to measurement of means for parameters of specific batches, and need not be the specific estimator method described above.

While the moving average method for monitoring calibration is a useful tool, its use is primarily directed toward monitoring loss of calibration due to slowly occurring phenomena such as electronic drift. However, step changes, i.e. abrupt changes, in calibration may result as a result, for example, of mechanical or electronic breakdown or clogging of fluid lines. The moving average method is specifically designed not to provide a rapid response to a step change calculating the value of the estimator employs a "smoothing" function.

It is desirable to provide a method and apparatus for hematology parameter measuring apparatus calibration monitoring which is both cost effective and responsive to long and short term changes in system calibration.

SUMMARY OF THE INVENTION

It is therefore an object of the present invention to provide an apparatus and a method in which calibration of a hematology parameter measuring apparatus is monitored through the use of a calculator and register system in which measured values are entered and which is responsive to step changes in calibration as well as gradual changes.

Briefly stated, in accordance with the present invention, there are provided a method and calculator-register apparatus system for monitoring calibration of hematology parameter measuring apparatus. The hematology parameter measuring apparatus provides hematological data which is entered in the calculator-register means for providing moving average values. Additionally, measured baseline parameter values of an unassayed sample obtained when the instrument was known to be in calibration are entered in register means. After a preselected length of time or number of sample runs on the instrument, the unassayed sample parameters are again measured and entered in the calculator-register means. The differences between the most recently measured values on the unassayed samples and the baseline values are calculated, and moving average values are obtained to provide an output which is indicative of the current calibration of the hematology parameter measuring apparatus.

BRIEF DESCRIPTION OF THE DRAWINGS

The means and method by which the foregoing objects and features of invention are implemented are pointed out with particularity in the claims forming the concluding portion of the specification. The invention, both as to its organization and manner of operation, may be further understood by reference to the following description taken in connection with the following drawings.

Of the Drawings.

DESCRIPTION OF THE PREFERRED EMBODIMENT

Figure 1:
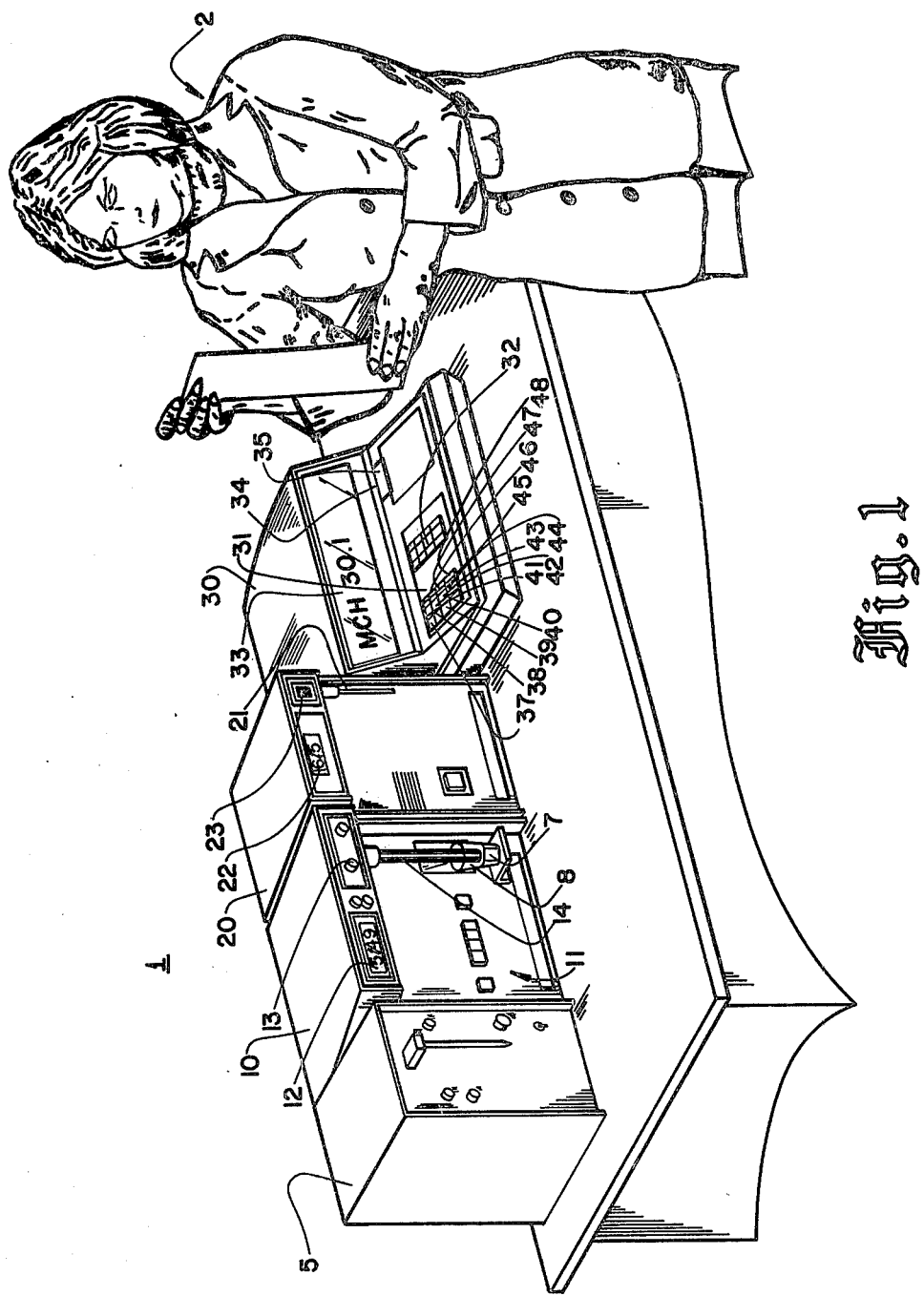
FIG. 1 is an illustration of a hematology parameter measurement system and calibration monitoring apparatus operated in accordance with the present invention.

Referring to FIG. 1, there is illustrated the hematology parameter measurement system 1 for use by an operator 2. The system 1 may take many different well-known forms. In the present embodiment, the system 1 comprises a diluter 5 for diluting blood samples on the order of 500:1 for white blood cell counts and 50,000:1 for red blood cell counts. Each sample dilution 7 is held in a sample container 8 which in FIG. 1 is shown in position on a cell counter 10. The cell counter 10 is a well-known cell counter which may provide outputs indicative of red blood cell count (RBC), white blood cell count (WBC) and hematocrit. Many forms of such counters are well-known in the art. The cell counter 10 includes function selection buttons 11, a display 12, and a calibration control 13. In practice, calibration control knobs are not actually mounted on front panels of counters since they are not adjusted frequently. However, the calibration control 13 is shown in an accessible position for facilitation of the present description. The cell counter 10 further includes an aperture tube 14 through which a sample dilution is drawn to produce pulses for counting in a well-known manner. For measurement of hemoglobin, a hemoglobinometer 20 is provided including a sample aspiration tube 21, a display 22, and a function control button 23. In the present system, the cell counter 10 is used to measure RBC, WBC and hematocrit. The values of these measurements are read individually from the display 12. Hemoglobin is measured on the hemoglobinometer 20 and the value for each sample is read from the hemoglobinometer display 22. Further values are calculated and quality control data is stored on a calculator-printer 30 which also includes means for registering selected measured values. The calculator-printer 30 calculates mean corpuscular volume (MCV), mean corpuscular hemoglobin (MCH) and mean corpuscular hemoglobin concentration (MCHC). It should be noted that allocations of tasks for parameter value generation between elements of the system 1 is a function of the particular types of measurement apparatus utilized. For example, the above task allocation will be followed when the counter 10 is for example, a Cell-Crit (R) Counter manufactured by Royco Instruments, Inc. of Menlo Park, Calif. However, if the counter 10 were an HC-500 (R) Counter manufactured by Hycel, Inc. of Houston, Tex., the value of MCV would be generated at the counter 10.

In the present embodiment, the calibration monitoring apparatus of the present invention is conveniently included in the calculator-printer 30. External features are further described with respect to FIG. 1, provision of printed information is described with respect to FIGS. 2 and 3, and internal features are described with respect to FIG. 4.

Referring in greater detail to the calculator-printer 30, there are provided first and second keyboards 31 and 32, a display 33 for displaying alphanumeric information indicative of function being performed or parameter being displayed as well as a value thereof, and a print station 34 for providing output information on a print card 35. The first keyboard 31 may conveniently comprise a readily commercially available 4×3 keyboard including twelve buttons 37–48. In a preferred form, the buttons 37, 38 and 39 may be used for commanding respectively display of the calculated parameters MCV, MCH and MCHC. The button 40 may be utilized for commanding the quality control routine further described below with respect to FIG. 3. Buttons 41–43 may be respectively utilized for enabling input of sample identification information, commanding printing and enabling date input. Button 44 may be utilized as an "enter" button for depression to enable entry of data. The buttons 45–48 are respectively utilized for enabling proper channeling of data indicative of the measured parameters RBC, hematocrit, WBC and hemoglobin in the circuit of FIG. 4. Data input is provided on the second keyboard 32, which may also comprise a 4×3 keyboard. Ten of the twelve buttons may each comprise a numeral 0–9, with the remaining two buttons being utilized for a decimal point and a "clear entry" button.

Figure 3:
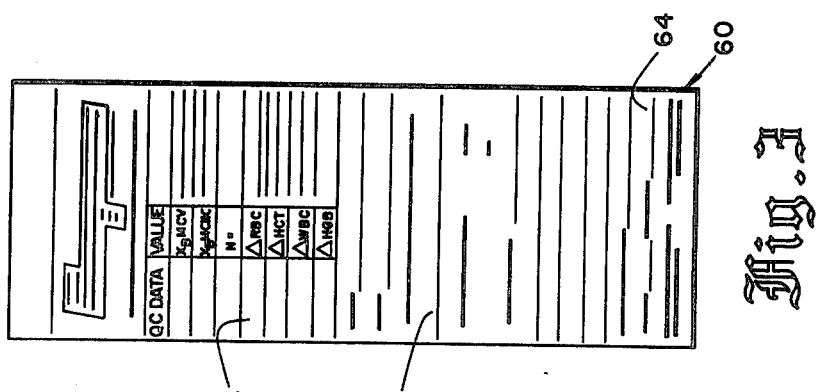
FIG. 3 is an illustration of a print card for quality control values.
Figure 2:
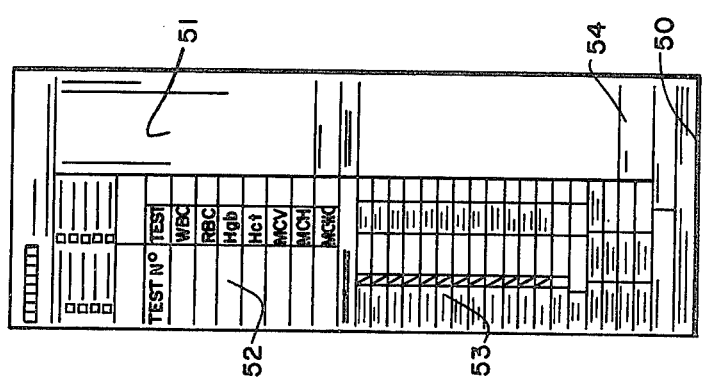
FIG. 2 is an illustration of a print card for hematology parameter values for a patient sample.

The print station 34 comprises a conventional printer system formatted to provide the entered data in an order on the print card 35. In FIGS. 2 and 3, there are respectively illustrated first and second forms of a print card 35 for use in the modes of operation of the printer-calculator 30. In FIG. 2, a sample data print form 50 is illustrated including an area 51 for patient identification and test identification. An area 52 is provided comprising columns and rows. A first column may be provided for entry of data, a second column may identify the parameter whose value is printed and the units associated with the value. A third column may include other information such as expected ranges of values for a test. A third area 53 may be provided for entry of additional information, for example, blood cell differential information and platelet counts. A fourth area 54 may be provided for time of day and operator identification. In FIG. 3, a quality control print card 60 is illustrated having an area 62 of columns and rows. A first column is utilized for entry of data at the print station 34, and a second column for identifying the value listed in the first column and a third column listing expected results. The first two rows in the area 62 are for recording moving average values for MCV and moving average for MCHC such as in accordance with the Bull et al method described above. The third row is for recording the number of samples in a batch. The fourth through seventh rows are for respectively recording differences between a baseline parameter values measured on what was described above as the unassayed sample and a value subsequently measured at a later time. This difference value may be performed for RBC, hematocrit, WBC and hemoglobin. Optionally, an area 63 may be provided for recording whether calibration action was required as described further with respect to FIG. 5 and for the operator recording of what action was taken. Similarly, an area 64 may be provided at a lower portion of the card 60 for recording operator information.

Figure 4:
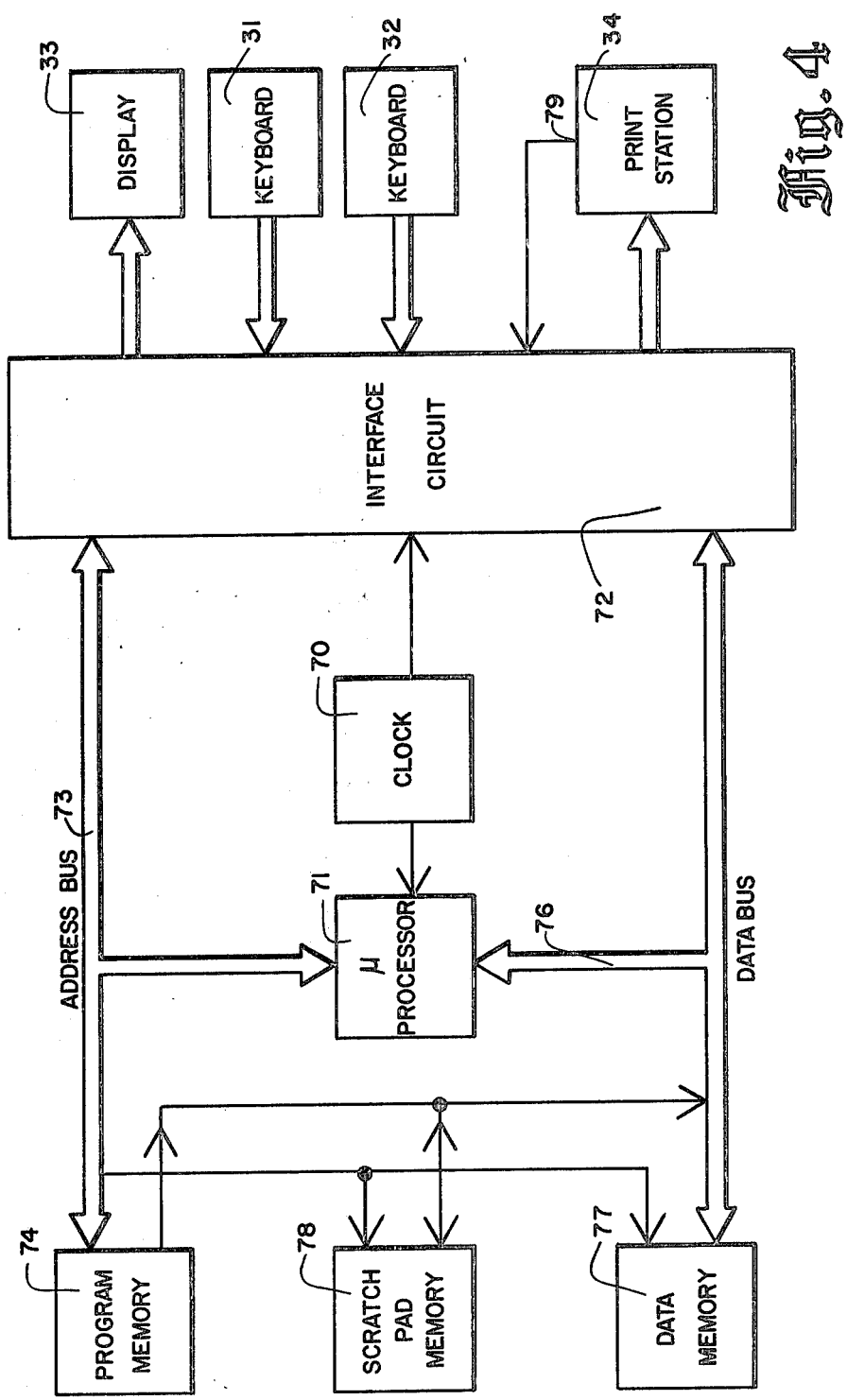
FIG. 4 is a block diagrammatic representation of the hematology data registering, calculating and printing apparatus for use in the present invention.

FIG. 4 is a block diagrammatic representation of the calculator-printer 30 The same reference numerals are used to describe elements corresponding to those in FIG. 1. The calculator-printer 30 includes a system clock 70 connected for synchronizing operations of a microprocessor 71 and interface circuitry 72. The microprocessor 71 and interface circuitry 72 are both "off the shelf" items. The microprocessor 71 may comprise, for example, the well-known M6800 or MOS6502. The microprocessor 71 receives instructions from and supplies instructions to an address bus 73 connected to both the interface circuit 72 and a program memory 74. A data bus 76 for carrying data interconnects the microprocessor 71, interface circuit 72 and a data memory 77. In addition, for calculations in a well-known manner, a scratch-pad memory circuit 78 is provided for receiving inputs from the program memory 74 and data memory 77 as well as for providing calculation results to the data memory 77. Additionally, of course, the program memory 74 supplies addresses for accessing data from the data memory 77. The actual programming of the microprocessor 77 and loading of the program memory 74 form no part of the present invention, but rather are straightforward applications of the operation described herein. It is well-known in the art that the desired operation is straightforwardly translatable without undue experimentation into program form and into selection of the particular hardware section of the many well-known available equivalents. This is illustrated by such publications as John J. Wester and William D. Simpson, *Software Design for Microprocessors* (Texas Instruments, Inc., Dallas, Tex., 1976) and the *M6800 Microprocessor Programming Manual* (Motorola, Inc., Phoenix, Ariz., 1975).

The keyboards 31 and 32 are connected to provide inputs to the interface circuit 72. Mode selection is made at the keyboard 31 and data is provided from the keyboard 32. The display 33 is connected to receive output data from the interface circuit 72. The print station 34 has an output line 79 for indicating the presence or absence of a print card 35 in the printer 34 connected to the interface circuit 72. In this manner, printing in the absence of a print card 35 being present is prevented. The print station is also connected to receive a print command and data from the interface circuit 72.

In operation, explained with reference to FIG. 1 as well as FIG. 4, the operator 2 prepares a dilution 7 in a sample container 8 at the diluter 5. It should be noted that separate dilutions 7 may be provided for red blood cell counts and white blood cell counts. Each dilution 7 is measured at the cell counter 10 which provides individual parameter results at the display 12. A dilution 7 is in a further sample container 8 is measured at the hemoglobinometer 20 to yield a result at the display 22. For entry of data, the operator 2 depresses the "ID" button 41. Consequently, a signal is provided from the keyboard 32 to the interface circuit 72 to result in an indication on the display 33 of an identification mode. The operator 2 enters numerals indicating the identity of a particular patient sample which are received in registers in the interface circuit 72 which are used to both store the numerical information and provide signals to display drivers so that the identification number is seen on the display 33. After the numerical information has been entered, the "enter" button 44 is depressed. A signal is provided from the keyboard 32 to the interface circuit 72 to command provision of the identification data to a preselected location in the data memory 77. The selection of memory location for the identification data also determines which memory locations in the data memory 77 are selected by the program memory 74 for storage of parameter values associated with the identification number entered. Similarly respective depression of the buttons 45, 46, 47 or 48 provide signals to the interface circuitry 72 to call forth display driver signals to indicate RBC, HCT, WBC or HGB on the display 33. A corresponding value read from the counter 10 or hemoglobinometer 20 is entered through the numerical keyboard 32. Signals indicative of the numerical information are stored in the interface circuit 72 and coupled to drive numerical elements in the display 33 to provide a display of the type seen in FIG. 1 including a parameter identity and numerical value. Upon depression of the "enter" button 44, the numerical value is entered into the memory location in the data memory 77 selected by the program memory 74 associated with the parameter and sample number to which it corresponds.

The entered parameter values are utilized as inputs in accordance with a conventional routine for calculation of the moving average values, preferably for MCV and MCHC. Also, calculated parameter values are obtained based on measured parameter values by operation of the microprocessor 71. The values MCV, MCH and MCHC are calculated in a conventional, well-known manner. MCV may be calculated as a scaling factor times hematocrit divided by RBC. MCH equals a scaling factor time hemoglobin divided by RBC, and MCHC is calculated as hemoglobin times a scaling factor divided by RBC. The individual parameter values MCV, MCH or MCHC may be viewed at the display 33 by respective depression of buttons 37, 38 or 39 to provide a signal to the interface circuit 72 to access the values from appropriate locations in the data memory 77. In order to provide a patient printout, a data print card 50 (FIG. 2) is inserted into the print station 34, and the sensing line 79 (FIG. 4) provides an enabling signal to allow printing. In order to print patient parameters, the operator 2 depresses the button 42, and information is provided in the format as shown in FIG. 2 on the card 50. Successive samples 7 are each processed in this manner.

Additionally, at the beginning of an operation period such as a multiple sample run, when the system 1 is known to be in calibration, the operator 2 selects one unassayed sample and performs parameter measurements. Each value obtained is established as a baseline value for the parameter to which it corresponds. The operator 2 depresses the ID button 41 and a numerical code indicative of a quality control sample is entered on the keyboard 31, to establish a baseline value storage mode, and enters the baseline values in the manner described above. In response to depression of the "enter" button 44, the baseline values are provided to memory locations dedicated by the program memory 74 for the storage thereof.

After a preselected number of samples have been run or after a predetermined period of time, the operator 2 may run a quality control check by testing another portion of the same one unassayed sample. Measurements are again taken in the manner described above. The I.D. button 41 is depressed, and a numerical code indicative of the quality control sample is entered on the keyboard 31. Depression of the "enter" button 44 results in storage of the measured values for calculations as described below.

The operator 2 inserts a print card 60 (FIG. 3) in the print station 34 to obtain a printout indicative of the moving value indices for MCV and MCHC as well as the number of samples over which the values were calculated. The data memory 77 includes a memory location to count the number of samples in a batch. Preferably, moving average calculations are made by computations of means for successive batches of twenty samples each. When the number of samples in a batch to the time of commanding of a quality control routine is less than twenty, the latest moving average value based on measurement of an entire batch is provided. Additional sample data is held in memory until twenty samples have been measured. The operator 2 determines if calibration is within predetermined limits through the running of a quality control mode initiated through depression of the button 40 to command the quality control mode.

Commanding of the quality control mode results in provision of the following information. Both the moving average values calculated for MCV and MCHC are accessed from respective locations in the data memory 77. Parameter difference values are calculated by accessing successive baseline values for each parameter that was measured and entered in response to first readings on the unassayed sample. Quality control values are also successively accessed from their memory locations for respective difference calculations of differences with respect to corresponding values of the baseline sample. In response to depression of the "print" button 42, each difference value is coupled through the interface circuit in turn to the print station 34. The moving average values and number of samples are also coupled in turn through the interface circuit 2 for printing of the card 60. The apparatus of the present invention provides indications on the print card indicative of both long term drift in calibration, the moving average values, and step changes in calibration, the difference values.

Figure 5:
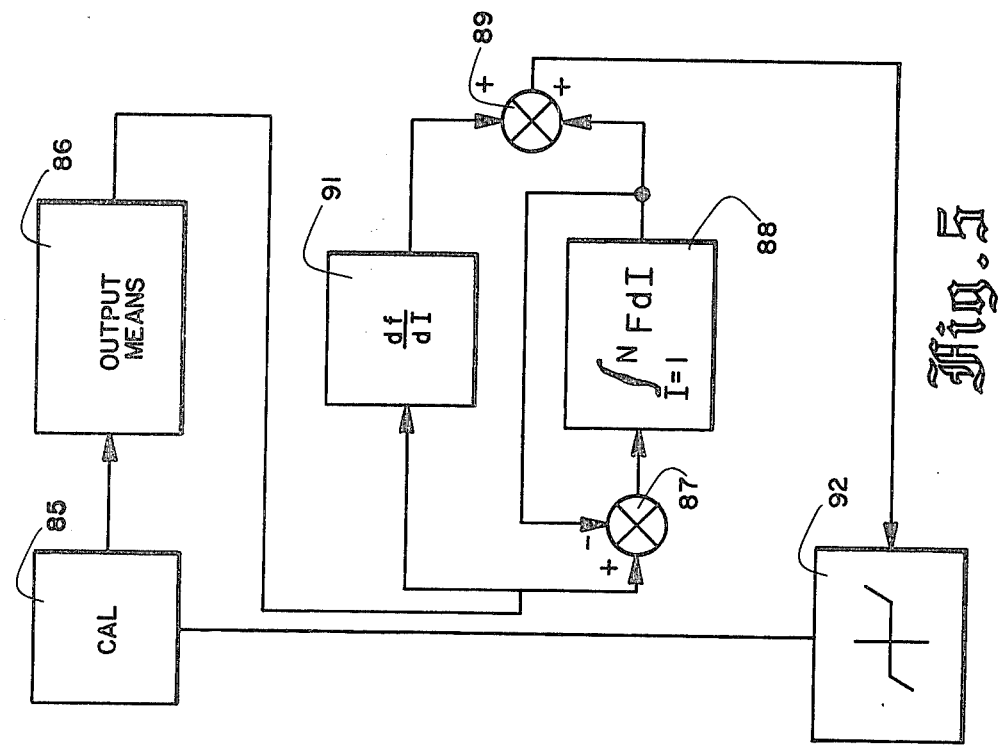
FIG. 5 is a functional flow diagram using servomechanistic representation useful in understanding the utilization of the present invention.

The use of the calibration monitoring method and system may be further understood by reference to FIG. 5 which is a servomechanistic block diagrammatic representation of the utilization of the present system. Calibration means 85 are connected to the output means 86 to determine the response of the output means 86 to a predetermined input. The output function of the output means 86 represents obtaining parameter measurements. The output of the output means 86 is coupled to an adding input of a summing junction 87 providing an output to a transfer function block 88 providing negative feedback to the summing junction 87 and an output to a further summing junction 89. The transfer function block 88 and the summing junction 87 provide a function equal to the integral of the function F with respect to I, where I is the particular sample being tested. The function F is the moving average function selected and calculated as described above. Additionally, the output means 86 provides an output to a transfer function block 91 for performing the function df/dI where I is the baseline reference control sample and f is one of the difference measurements between the baseline values obtained for the unassayed sample and the later measurement of the unassayed sample. The function block 91 also provides an output to the summing junction 89 indicative of the magnitude of change in measurement of the control sample. The summing junction 89 provides an output to a discriminator 92 which may comprise a threshhold circuit or the operator 2. The discriminator 92 is shown as providing no response when the output levels from the summing junction 89 are within a preselected range of a zero value. This is to say that no recalibration is necessary when changes in the measured moving average or difference measurements are within calibration tolerances. However, when the absolute value of the calibration difference as manifested by the output of the summing junction 89 is above a predetermined level, recalibration is indicated. Recalibration is then done by convenient means, and thus an output line from the discriminator 92 to the calibration circuit 85 is shown for maintaining the system in calibration. In the embodiment of FIG. 1, the calibration means comprises the control 13 on the counter 10. And the operator 2 may perform the discrimination function.

What is thus provided is a method and means for monitoring calibration of a hematology parameter measurement system. A system is provided in which a smoothed function is generated and which a differential function capable of responding to step changes is also generated and wherein all functions are monitored for an indication of the necessity for recalibration. Thus, the system may respond to both short term errors causes such as aperture blockage and long term error sources such as electronic drift. The calibration monitoring apparatus need not necessarily be included in the calculator-printer 30, although it is contemplated that will be most desirable in most applications. The specification has been written with a view toward enabling those skilled in the art to make departures from the specific embodiment disclosed to provide a method and apparatus in accordance with the present invention.

What is claimed as new and desired to be secured by Letters Patent of the United States is:

1. A calculator-register apparatus for monitoring calibration of hematology parameter measurement apparatus for performing measurements on test samples comprising: means for receiving parameter measurements on successive test samples and generating a moving average value for at least one parameter, means for storing a baseline value of at least one parameter measured in response to a baseline sample tested when said measurement apparatus is known to be in calibration, means for storing entry of a subsequent value of said at least one parameter measured on said baseline sample after a predetermined duration of operation, means for calculating a difference value between said baseline reading on said baseline sample and said subsequent value for each said at least one parameter, and means for accessing values coupled to said means for receiving parameter measurements and to said means for calculating, said means for accessing values being actuated in response to a command for providing outputs indicative of said moving average value and said difference readings, whereby an indication of necessity for recalibration is provided by said moving average value and said difference value.

2. Apparatus according to claim 1 comprising an interface circuit, and means for selecting a mode of operation and data entry means each connected, to said interface circuit said interface circuit being coupled to said means for receiving parameter measurements and generating a moving average value, and being connected to said means for storing and to said means for calculating and wherein the mode of operation is defined by a set of interconnections therebetween.

3. Apparatus according to claim 2 comprising first keyboard means comprising said means for selecting a mode of operation, second keyboard means comprising said data entry means and wherein said first keyboard means comprises a quality control mode selection means for selectively initiating the provision of said outputs indicative of said moving value average and said difference values for provision to utilization means.

4. Apparatus according to claim 3 further comprising utilization means comprising a print station coupled to said interface circuit for printing on a card indicia corresponding to the parameters whose values are indicated by the data supplied to said print station, said first keyboard means comprising means for selectively commanding a print mode, said print station being operable in response to a print command entered on said first keyboard means.

5. In a hematology parameter measurement system including means for measuring hematological parameters, means for monitoring calibration comprising means for providing a moving average value in response to measurement of successive values of at least one parameter to which an estimator function is applied, means for storing a baseline and a subsequent parameter value for an unassayed control sample and for providing a difference signal indicative of the difference therebetween, and means for selectively providing in a quality control mode an indication of said moving average value and difference value, whereby an indication of necessity for recalibration is indicated.

6. The method for monitoring calibration of a hematology parameter measurement apparatus, measuring sample parameters on said apparatus, recording values obtained by the step of measuring, calculating a moving value index for at least one parameter by use of an estimator function on said values, taking at least one parameter measurements on one preselected sample to obtain at least one baseline parameter measurement and storing said at least one baseline parameter measurement, measuring said at least one parameter for said preselected sample after a predetermined duration of operation to obtain at least one subsequently measured value, generating a difference value indicative of the difference between each said at least one baseline value and each corresponding said at least one subsequently measured value, and selectively providing an indication of said moving average index and of said difference value for indicating of need for calibration.

* * * * *